United States Patent [19]

Aichinger

[11] Patent Number: 5,148,460
[45] Date of Patent: Sep. 15, 1992

[54] AUTOMATIC X-RAY EXPOSURE UNIT

[75] Inventor: Horst Aichinger, Fuerth, Fed. Rep. of Germany

[73] Assignee: Siemens Aktiengesellschaft, Munich, Fed. Rep. of Germany

[21] Appl. No.: 734,565

[22] Filed: Jul. 23, 1991

[30] Foreign Application Priority Data

Aug. 24, 1990 [EP] European Pat. Off. ........ 90116267.7

[51] Int. Cl.⁵ .............................................. H05G 1/44
[52] U.S. Cl. .................................... 378/108; 378/37; 378/95
[58] Field of Search .............. 378/37, 95, 96, 97, 378/101, 108, 162, 207

[56] References Cited

U.S. PATENT DOCUMENTS

| | | | |
|---|---|---|---|
| 2,983,819 | 5/1961 | Bigelow et al. | 378/108 |
| 4,034,222 | 7/1977 | Azam et al. | 378/97 |
| 4,097,741 | 6/1978 | Pfeiler et al. | |
| 4,189,645 | 2/1980 | Chaney et al. | |
| 4,260,894 | 4/1981 | Neumann | |
| 4,455,669 | 6/1984 | Aichinger et al. | |
| 4,744,099 | 5/1988 | Hoettenrauch et al. | 378/95 |
| 4,763,343 | 8/1988 | Yanaki | 378/95 |

Primary Examiner—David P. Porta
Attorney, Agent, or Firm—Hill, Van Santen, Steadman & Simpson

[57] ABSTRACT

An automatic x-ray exposure unit has first and second radiation detectors disposed sequentially and in registry in the direction of radiation propagation following the examination space. Each radiation detector is formed by a matrix of detector elements, also in registry. The detector elements are connected to a computer which calculates the quotient of the signals of each pair of detector elements in the first and second radiation detectors which are in registry. Those pairs of detector elements having a signal quotient which is above a predetermined threshold are automatically taken into consideration for selecting the measuring field for an x-ray exposure.

1 Claim, 2 Drawing Sheets

AUTOMATIC X-RAY EXPOSURE UNIT

BACKGROUND OF THE INVENTION

1. Field of the Invention

The present invention is directed to an automatic x-ray exposure unit, and in particular to an exposure unit suitable for use in mammography.

2. Description of the Prior Art

In x-ray technology, for example in mammography, a detector for the automatic exposure unit is generally arranged behind the film-foil system. In conventional automatic x-ray exposure units, this results in the exposure to which the examination subject is subjected being dependent on the subject thickness. An automatic transparency matching is possible if, as disclosed in German OS 30 08 261, a detector having two detector elements is used, with the radiation incident on each detector element being differently filtered, and the quotient of the signals from the detector elements is formed. This quotient is thus a transparency-dependent signal, which can be used for balancing the automatic exposure unit.

Despite the automatic transparency matching, an optimal exposure only results in this known system when the position of the measuring field can be brought into coincidence with the densest region of the mammory gland.

SUMMARY OF THE INVENTION

It is an object of the present invention to provide an automatic x-ray exposure unit which makes use of two radiation detectors and which forms a quotient signal, wherein the position of the measuring field is automatically and optimally selected.

The above object is achieved in accordance with the principles of the present invention in an automatic x-ray exposure unit having first and second radiation detectors disposed in sequence in the direction of beam propagation following the examination space, each radiation detector being formed by a matrix of detector elements and being disposed so that the detector elements are in registry, forming detector element pairs. The detector elements are connected to a computer which calculates the quotient of the signals for each pair of detector elements and only those pairs of detector elements having quotients which are above a predetermined threshold are automatically taken into consideration for selecting the measuring field for an x-ray exposure. Those detector elements having an output signal quotient which is below the prescribed threshold are assumed to be disposed behind less dense subject regions, and are therefore automatically shut off. The measuring field, consequently, is automatically placed behind the densest region of the mammory gland. Detector elements which are impinged by direct radiation (i.e., radiation unattenuated by the examination subject) are also shut off.

DESCRIPTION OF THE PREFERRED EMBODIMENTS

Figure 1:
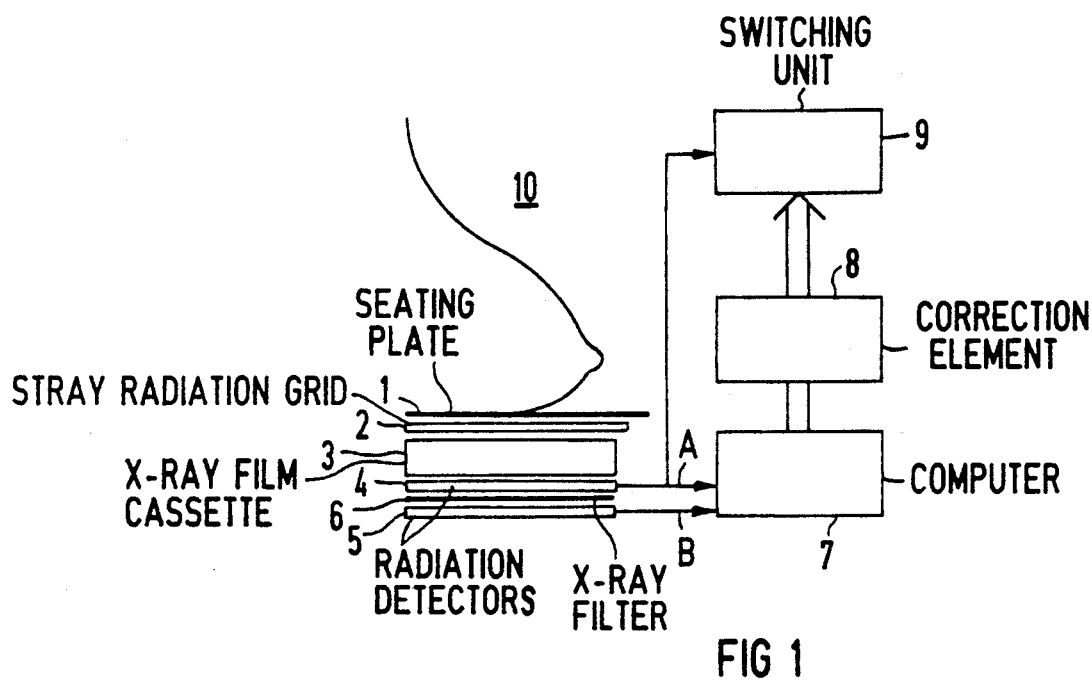
FIG. 1 is a schematic block diagram of an automatic x-ray exposure unit constructed in accordance with the principles of the present invention.

An automatic x-ray exposure unit constructed in accordance with the principles of the present invention is shown in FIG. 1, which is suitable for mammography. The exposure unit includes a seating plate 1, on which an examination subject, such as a mammory gland, is placed in an examination space 10 where it can be irradiated with x-rays from a source (not shown). The automatic exposure unit also includes a stray radiation grid 2, an x-ray film cassette 3, and first and second radiation detectors 4 and 5, separated from each other by an x-ray filter 6. The radiation detectors 4 and 5 are disposed in sequence in the direction of radiation propagation, and are also disposed in registry. The detectors 4 and 5 are connected to a computer 7 which, via a correction element 8, controls a switching unit 9 of the automatic exposure unit in accordance with the respective subject transparency.

Figure 2:
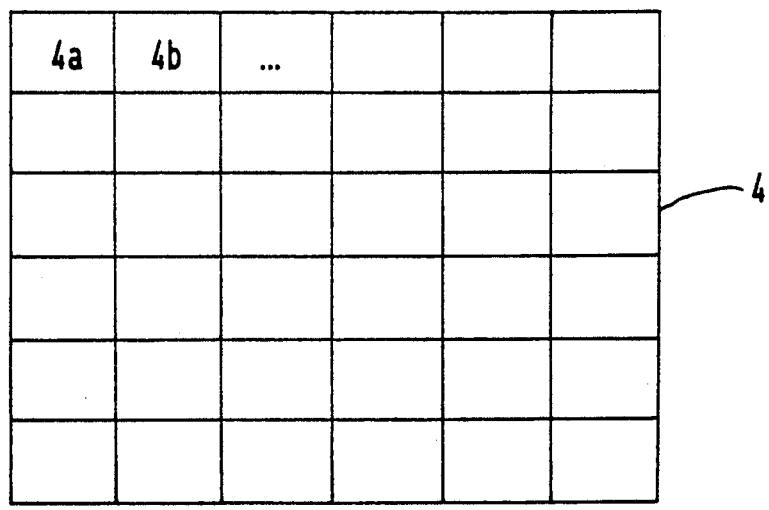
FIG. 2 is a plan view of one detector in the x-ray exposure unit of FIG. 1.

A plan view of the detector 4 is shown in FIG. 2. The detector 4 consists of a matrix of individual detector elements 4a, 4b, etc., which are individually connected to the computer 7. The detector 5 is identically constructed. Since the detectors 4 and 5 are in registry, the individual detector elements thereof are also in registry. Respective elements in the detectors 4 and 5 which are in registry will be referred to herein as a detector element pair.

The area of the detectors 4 and 5 extends over the entire film format. The individual detector elements 4a, 4b, etc. may having a size, for example, of 3 cm × 4 cm.

During an exposure, each detector element 4a, 4b, etc. (and each detector element of the detector 5) supplies an output signal corresponding to the incident radiation intensity. The computer 7 forms a quotient for each detector element pair. This quotient is a measure for the subject thickness disposed in the exposure space 10 in front of the detector element pair.

Figure 3:
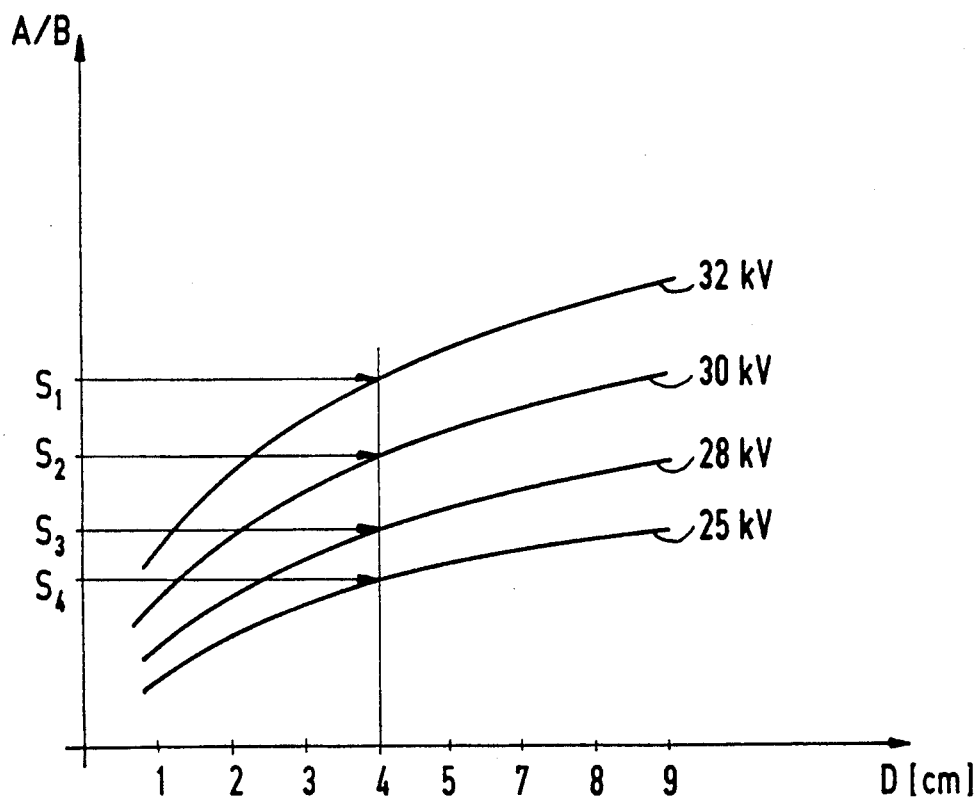
FIG. 3 is a graph showing a set of curves for explaining the operation of the apparatus in FIGS. 1 and 2.

The dependency of this quotient A/B on the subject thickness D for four different x-ray tube voltages is shown in FIG. 3. Given a defined x-ray tube voltage, the signal A/B increases with the subject thickness of the respectively preceding subject region. The signal will also increase dependent on the subject density, i.e., ultimately dependent on the transparency.

An automatic selection of the measuring field ensues by setting a quotient threshold S1, S2, S3, or S4. Only those detector elements which belong to detector element pairs whose signal quotient is above the selected threshold S1 through S4 are enabled for the actual measurement. The other detector elements, i.e., those in pairs whose signal quotient is below the selected threshold, are disenabled. Given, for example, an x-ray tube voltage of 32 kV, only those pairs of detector elements having an output signal quotient above the threshold S1 are enabled. This corresponds, for example, to a thickness or a transparency corresponding to 4 cm of plexiglass. In this manner, the measuring field selected for the automatic exposure unit always lies behind the thickest or densest subject region, i.e., behind the subject region having the lowest transparency.

After selection of the measuring field has been concluded during an exposure, an aggregate signal of the detector elements 4a, 4b, etc., of the detector 4 in the selected measuring field is used for deactivating the exposure. Deactivation ensues via the switching unit 9 to which this aggregate signal is provided. An average value of the quotient signals in the selected measuring field is used for correcting the prescribed value of the shut-off dose of the switching unit 9.

Although modifications and changes may be suggested by those skilled in the art, it is the intention of the inventor to embody within the patent warranted hereon all changes and modifications as reasonably and properly come with the scope of his contribution to the art.

I claim as my invention:

1. An automatic x-ray exposure unit, for use with a source of x-radiation, said automatic exposure unit comprising:

first and second radiation detectors disposed in sequence and in registry in a radiation propagation direction following an examination space, each radiation detector consisting of a matrix of detector elements also in registry with respective detector elements in registry forming a plurality of detector element pairs, each detector element generating an output signal corresponding to the intensity of radiation thereon;

computer means connected to each of said detector element pairs for calculating a quotient of the output signals of each detector element in each detector element pair; and means for automatically selecting a measuring field for an x-ray exposure which includes only those detector element pairs having a quotient above a predetermined threshold.

* * * * *